United States Patent [19]
Johnson et al.

[11] Patent Number: 5,522,798
[45] Date of Patent: Jun. 4, 1996

[54] CONTROL OF A MULTI-CHANNEL DRUG INFUSION PUMP USING A PHARMACOKINETIC MODEL

[75] Inventors: Noel L. Johnson, San Jose; Jyh-yi T. Huang, Sunnyvale; Tao Chang, Saratoga, all of Calif.

[73] Assignee: Abbott Laboratories, Abbott Park, Ill.

[21] Appl. No.: 324,392

[22] Filed: Oct. 17, 1994

[51] Int. Cl.⁶ .................................................. A61M 31/00
[52] U.S. Cl. ........................................................... 604/65
[58] Field of Search ........................... 604/30, 31, 49, 604/53, 65–67, 246, 247, 151, 118

[56] References Cited

U.S. PATENT DOCUMENTS

| | | | |
|---|---|---|---|
| 4,213,175 | 7/1980 | Kurihara | 364/119 |
| 4,559,037 | 12/1985 | Franetzki et al. | 604/151 |
| 4,594,326 | 6/1986 | Wade | 436/501 |
| 4,710,864 | 12/1987 | Li | 364/148 |
| 4,723,958 | 2/1988 | Pope et al. | 604/890.1 |
| 4,731,051 | 3/1988 | Fischell | 604/67 |
| 4,898,578 | 2/1990 | Rubalcaba, Jr. | 604/66 |
| 5,010,473 | 4/1991 | Jacobs | 364/150 |
| 5,072,660 | 12/1991 | Helbling | 99/280 |
| 5,078,683 | 1/1992 | Sancoff et al. | 604/67 |

*Primary Examiner*—Corrine M. Maglione
*Assistant Examiner*—Manuel Mendez
*Attorney, Agent, or Firm*—Ronald M. Anderson

[57] ABSTRACT

A host controller (10) selectively predicts and controls drug concentrations for each of a plurality of channels delivered through multiple drug channels of a multi-channel drug delivery system. The host controller includes a controller (32) that is coupled to each drug channel of the multi-channel drug delivery system to receive actual drug delivery rate information. Delivery of each drug can be selectively separately controlled by a PK model (the same PK model for each channel or different PK models for different channels) to achieve either a desired setpoint for a blood plasma drug concentration or a setpoint for an effect compartment drug concentration. Control of the drug delivery by the PK model can be selectively interrupted during operation of the multi-channel drug delivery system, to switch to a manual mode in order to administer a bolus dose or a continuous infusion, and then, control of drug infusion using the PK model can be subsequently resumed. The blood plasma and/or effect compartment drug concentrations for any drug predicted in accordance with a PK model are selectively displayed to a user on an electroluminescent (EL) display (36), even during operation of the multi-channel drug delivery system in the manual mode, or after the drug delivery has been terminated. Prediction of drug concentration is tracked for each drug administered, enabling multiple drugs to successively administered in the same drug channel and control of a drug delivery by the PK model to continue when the drug channel used to administer the drug is changed.

55 Claims, 5 Drawing Sheets

5,522,798

CONTROL OF A MULTI-CHANNEL DRUG INFUSION PUMP USING A PHARMACOKINETIC MODEL

FIELD OF THE INVENTION

The present invention generally pertains to a multi-channel drug infusion system that is capable of infusing a plurality of drugs into a patient, and more specifically, to a method and apparatus for controlling the multi-channel drug infusion system.

BACKGROUND OF THE INVENTION

In recent years, microprocessor controlled drug infusion systems have become relatively common. A typical control for a drug delivery system includes a keypad or other user interface enabling a medical practitioner to enter the rate of drug delivery, duration, and volume of a drug or medicinal fluid to be infused into a patient. Drug delivery is normally either programmed to occur as a continuous infusion or as a single bolus dose.

It is not uncommon for a plurality of different drugs to be prescribed for intravascular delivery to a patient, either in a sequence, or simultaneously. Although two or more pumps can be employed to infuse a plurality of drugs, there are several clear advantages to using a single multi-channel pump for this purpose. Simply minimizing the number of separate drug delivery pumps and the concomitant hardware that must be connected to the patient in order to simultaneously administer several different drugs is probably adequate justification for use of a multi-channel drug infusion system, but there are other more important advantages. For example, certain drugs are chemically incompatible. The controller of a multi-channel drug delivery system can be programmed to flush a common drug delivery line with a saline fluid between infusion of two incompatible drugs and to warn medical personnel of the potential problem if simultaneous infusion of the two drugs is attempted. It is also much easier to program a complete drug delivery regimen on a single control instead of programming several different drug delivery systems.

Although conventional drug infusion controllers have greatly improved the efficiency and ease with which drugs are delivered to a patient, medical personnel must still enter the rate and volume that is appropriate for the specific drug to be infused, to achieve a desired effect. In many cases, the physician will want to quickly achieve a desired blood plasma concentration of a drug and then maintain that concentration for a defined period of time. The blood plasma concentration that will result from a given rate of drug infusion depends upon certain characteristics of the patient, such as age, weight, and gender. Accordingly, the physician will typically rely upon prior experience with a drug or be forced to consult reference materials to determine the rate at which a drug should be delivered. Initially, the physician may program the drug infusion system to deliver a bolus of the drug, followed by a continuous infusion at a lower rate, and then, may adjust the delivery rate based upon the apparent effect of the drug on the patient. With considerable experience, a physician may be able to accurately estimate the proper rate settings to achieve the desired effect by a particular drug. However, in many cases, the physician's initial estimate of the appropriate rate of drug delivery will need to be modified several times, based upon the observed effect of the drug on the patient. Given the computational power of the microprocessors typically used for controlling an infusion system, it should be possible for the control to automatically determine the rate of drug infusion to achieve a desired drug concentration.

U.S. Pat. No. 5,010,473 (Jacobs) discloses a model based open-loop process for controlling the concentration of a drug delivered intravenously to a patient as a function of the rate of infusion. A three-compartment pharmacokinetic (PK) model is used to determine the plasma drug concentration. Based upon the linear relationship between data pairs comprising a rate of infusion and a corresponding plasma drug concentration, an interpolated rate is determined by a microprocessor as a function of the specified plasma drug concentration. The actual infusion rate of the drug during successive time intervals is repetitively used to compute the plasma drug concentration at the end of each time interval. For each iteration, state variables from the previous computation are applied to determine the next interpolated infusion rate. The open-loop control method disclosed by Jacobs rapidly achieves the specified plasma drug concentration.

It will be apparent that controlling the administration of a plurality of drugs through a multi-channel drug infusion system using a PK model to predict the drug concentration and control the rate of infusion would provide significant advantages over the prior art control of a single channel. If desired, a different PK model could then be selectively applied to control the delivery of each different drug through each channel of a multi-channel drug delivery system, or the same model could be used for the control of each channel of the system.

A PK model control for a pump should have other features not common found in the prior art devices. For example, a physician should be able to selectively use a PK model for controlling drug administration to achieve a desired effect of a drug on the patient, instead of simply achieving a desired blood plasma drug concentration. PK models such as that disclosed in the above-cited Jacobs patent model the movement of drugs within the patient's body in terms of a plurality of compartments. Such a model can be adapted to include an effect compartment that hypothetically corresponds to the actual effect of the drug on a patient. By predicting the effect compartment drug level, it should be possible for the model to better control the rate of drug delivery. A physician is generally more concerned with obtaining the desired effect of the drug on the patient than with achieving some arbitrary blood plasma drug concentration.

At times, a physician may find it necessary to briefly alter the parameters of a drug therapy. If the drug administration is being controlled by a PK model, the physician may want to switch to a manual mode for a period of time, for example, to administer a bolus dose. It should thereafter be possible to switch back to the PK model controlled mode. Accordingly, it is important that the control for a pump that is used to administer drugs in accordance with a PK model be able to track the history of the drug administered and take into consideration changes that occur while the PK model controlled mode is interrupted by a manual controlled mode, when the PK model control mode resumes. Since the history of the blood plasma concentration must be retained to achieve this goal, the infusion system control should be able to display both historical and predicted blood plasma and compartment effect drug concentrations levels to medical personnel for each drug administered, during either model controlled or manual controlled modes of operation. The model should continue to track and display these parameters, even after the drug infusion has stopped, so long as the patient's case is active.

SUMMARY OF THE INVENTION

In accordance with the present invention, a control is defined for a multi-channel drug delivery system with which a plurality of drugs are selectively administered to a patient through a plurality of drug channels in accordance with a PK model. The control includes a processor that is controlled in accordance with a set of program instructions that determine the steps of the PK model. A memory, coupled to the processor, stores the set of program instructions and a plurality of parameters used in the PK model, and a display, which is coupled to the processor, displays the parameters and data indicative of a state of the PK model. Also coupled to the processor is a user interface. The user interface enables a user to enter at least some of the plurality of parameters used by the PK model in controlling administration of each drug to the patient and includes identification means for identifying the drug that is being administered in each of the drug channels. PK model prediction means, embodied in the processor executing the set of program instructions, determine a drug concentration within the patient over time for each drug, as the drugs are administered by the multi-channel drug delivery system. The drug concentration is determined during any interruption and after any termination of a drug delivery, and regardless of any change in the drug channel through which a specific drug is delivered.

The processor is controlled by the program instructions to selectively model and control either an effect compartment drug concentration level, or a blood plasma drug concentration of the drug in the patient. The memory stores blood plasma drug concentrations over time for the plurality of drugs, and the display selectively shows at least one of a predicted and a historical blood plasma drug concentration over time for the plurality of drugs. Similarly, the memory stores effect compartment drug concentrations over time for the plurality of drugs, and the display can selectively show at least one of a predicted and a historical effect compartment drug concentration of the plurality of drugs over time.

The user interface includes a mode switch enabling the user to select between a manual mode and a PK model control mode for controlling the delivery of any of the plurality of drugs by the multi-channel drug delivery system. While operating in the manual mode, the processor continues to model and track at least one of a blood plasma drug concentration and an effect compartment drug concentration over time, thereby enabling the processor to control the administration of a drug in the PK model control mode when that mode is selected after the manual mode was used to control delivery of the drug by the multi-channel drug delivery system. During operation of the multi-channel drug delivery system in the manual mode, the display shows the blood plasma drug concentration and/or the effect compartment drug concentration. In addition, even though operating in the manual mode, the display shows at least one of a historical and a predicted blood plasma drug concentration level over time, and/or at least one of a historical and a predicted effect compartment drug concentration over time. After delivery of a drug is terminated, or after delivery of the drug is resumed in a different drug channel, or after a different drug is delivered in the same drug channel as the drug and then delivery of the drug is resumed in that drug channel, the display continues to show: (a) at least one of the historical and predicted blood plasma drug concentrations over time, or (b) at least one of the historical and predicted effect compartment drug concentration over time.

A further aspect of the present invention is also directed to a control for a multi-channel drug delivery system with which a plurality of drugs are selectively administered to a patient in accordance with a PK model. This control generally includes the same components as the above-described control. However, the user interface includes a selector switch that selectively determines whether the control uses the PK model to achieve a desired blood plasma drug concentration, or a desired effect compartment drug concentration. A similar control is also defined for use with a drug delivery system that delivers a drug to a patient (i.e., a drug delivery system that is not necessarily multi-channel).

Still further aspects of the present invention are directed to methods for controlling drug delivery systems. The steps of each method are generally consistent with the functions of the components used to achieve the different aspects of the control discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Multi-Channel Drug Delivery System and Host Controller

Figure 1:
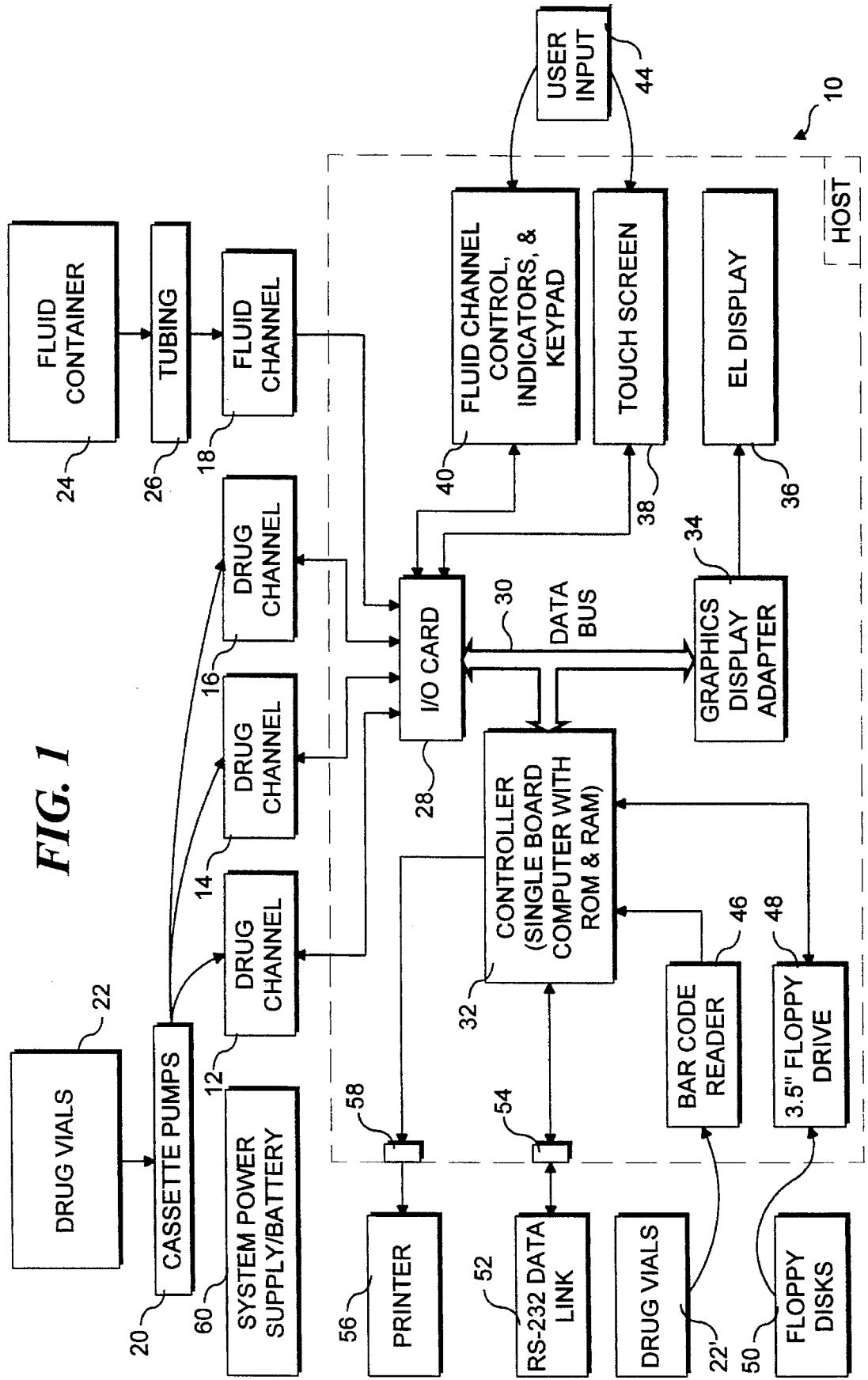
FIG. 1 is a block diagram of a multi-channel drug delivery system, and of a host controller for the multi-channel drug delivery system, in accordance with the present invention.

With reference to FIG. 1, the components of a host controller 10 are disclosed, in connection with a multi-channel drug delivery system that includes three "drug channels" 12, 14, and 16 and a "fluid channel" 18. For purposes of this disclosure, the term "drug channel" refers to an independent path through which a drug is delivered to a patient from a source container, either through a separate line or to a manifold (not shown), from which one or more drugs are infused into the patient. The drugs are separately input to the manifold through one-way check valves and then flow through a common line to the patient from an outlet of the manifold. The term "fluid channel," as used herein, refers to a path through which a fluid is delivered to the manifold from a source and then to the patient. The patient typically receives the drugs intravenously, but other types of drug infusion are contemplated.

In the preferred embodiment, host controller 10 is integrally housed with the multi-channel drug delivery system and is linked thereto by a plurality of electrical paths. Although host controller 10 can readily be adapted for controlling other types of multi-channel drug delivery systems, and for use in controlling a single drug channel delivery system, in the preferred embodiment discussed below, it controls from one to three cassette pumps 20 that dispense drugs to the patient in a liquid form. Fluid channel 18 is used for administering a hydration liquid and/or for flushing the manifold and the common line that delivers the drugs to the patient from the manifold.

The multi-channel drug delivery system shown in FIG. 1 accepts separate drug vials 22 as the source of the drugs administered through the drug channels. Pump cassettes 20 are like those sold by Abbott Laboratories for use in its LifeCare 5000™ and comprise a plastic housing with passages, valves, and chambers through which liquid flows as a piston displaces an elastomeric membrane accessed through a pumping port formed in the cassette housing. Each of the three drug channels 12–16 are able to deliver liquid drugs to a patient at a rate in the range from 0.1 ml to 1200 ml per hour; however, pumps having substantially different delivery rates can also be used with the present invention. Since details of the actual pumping mechanism used play no role in the present invention, they are not separately shown in the drawing figures nor further discussed. It is sufficient that the reader understand that each drug channel 12–16 has a cassette pump 20 for separately administering a liquid drug to the patient. More importantly in the present invention is the fact that operation of the cassette pumps in each of the drug channels is controlled by host controller 10, which operates in three different modes, as selected by a user.

Fluid channel 18, which is also controlled by host controller 10, infuses hydration fluid from a fluid container 24 into the patient through tubing 26. Preferably, fluid channel 18 comprises a volumetric pump, such as that sold by Abbott Laboratories under the trademark LifeCare 175™.

Each of the three drug channels and the fluid channel are controlled through electrical signals conveyed through an input/output (I/O) card 28. I/O card 28 is electrically connected to the three drug channels and fluid channel 18 so that control signals can be sent to the cassette pump in each of the drug channels (and to the pump in the fluid channel) and so that data signals can be received from the drug channels. The signals received from the drug channels indicate alarm conditions, sensor conditions, and most importantly for the present invention, the actual rate at which a drug is being delivered to a patient through the drug channels. These signals pass through I/O card 28 and through a data bus 30 into a controller 32. Controller 32 comprises a single board computer. In the preferred embodiment, controller 32 includes an Intel Corporation microprocessor or central processing unit (CPU), Model 80286 (not separately shown), although other types of CPUs can be used. Also included on controller 32 and coupled to the CPU are both random access memory (RAM) and read only memory (ROM), along with other conventional integrated circuits used on a single board computer as are well known to those of ordinary skill in the art. Single board computers suitable for use in the present invention are available from many different sources.

Controller 32 is coupled through data bus 30 to a graphics display adapter 34. In the preferred embodiment, this graphics display adapter comprises a conventional video graphics adapter (VGA), of the type commonly used in personal computers. The graphics display adapter is coupled to an electroluminescent (EL) display panel 36 on which instructions and data are presented to a user in both textual and graphic format. In addition, a touch screen 38 is coupled to I/O card 28 for accepting input from a user. The input is converted into signals conveyed on data bus 30 to controller 32. Additional information is presented to the user and selection and input of various parameters is enabled on a fluid channel control and front panel indicator panel 40, which is also coupled to controller 32 via I/O card 28 and data bus 30.

Fluid channel controls and front panel indicator panel 40 includes a 16-button keypad and a plurality of light emitting diodes (LEDs) (not separately shown). As shown in a block 44, user input is applied to control the operation of the multi-channel drug delivery system by selections made on touch screen 38 and by entry of parameters using the keypad. The user input determines the control mode of the host controller for each drug channel. Two modes of drug delivery are provided, including a manual mode in which the multi-channel drug delivery system is used to administer either a bolus dose or a continuous infusion at a predefined rate, and a PK model controlled delivery mode. In the PK model controlled delivery mode, a desired setpoint is automatically achieved by controlling the multi-channel drug delivery system to attain the desired setpoint based upon a predicted drug concentration within the patient produced by the model. The predicted concentration of each drug administered by the multi-channel drug delivery system is continuously modeled throughout an entire patient case, regardless of: (a) the control mode that is selected, (b) any interruption of the drug delivery that may have occurred, or (c) termination of the drug delivery. The PK model control mode can thus be initiated at any time, interrupted, and then resumed. A first drug can be administered through one drug channel under the PK model mode or manual mode, a different second drug can then be administered through that drug channel, and the administration of the first drug can be resumed through the same or a different drug channel under the PK model control mode. Accordingly, even through only three drug channels are provided in the multi-channel drug delivery system disclosed above, controller 32 can continue to track the predicted drug concentrations of substantially more than three drugs administered to the patient, and can resume or initiate control of the delivery of any of the drugs using the PK model control mode at any time. Thus, a plurality of different drugs can be administered to a patient through any one or more of the drug channels, and PK control of the administration of any of those drugs can be selectively assumed by the controller at any time during the patient case.

On the touch screen, a user enters the age, weight, gender, and other patient specific parameters or drug parameters (if not stored in the memory of controller 32) that a PK model may require for predicting the drug concentration and selectively controlling the rate at which each drug is delivered to the patient. The user can also selectively determine the information that is displayed on EL display 36 for any drug administered during a patient case, including the prior drug concentration at any past time, the current drug concentration, and a predicted drug concentration at a specified future time. In addition, the user input can selectively determine the PK model that will be applied to model each different drug that is administered (i.e., different PK models can be used for each drug), and can selectively determine whether the delivery rate will be controlled by the PK model to achieve either a user entered blood plasma drug concentration setpoint or effect compartment drug concentration setpoint.

To load a control program (or program updates or drug modeling data) into the memory of controller 32, host controller 10 includes a 3½ inch floppy drive 48. A floppy disk 50 can be inserted into drive 48 to download program files or data, or to receive patient history data for archival storage. The ROM on controller 32 is of the electrically erasable programmable read only memory (EEPROM) type so that drug parameter data used in the PK model for controlling the multi-channel drug delivery system can be downloaded from a floppy disk and stored therein.

The specific drug that is being administered by one of the drug channels could be identified with an entry by the user on the keypad or on the touch screen of the user interface. However, to simplify identification of the drugs being infused by the multi-channel drug delivery system, a bar code reader 46 is preferably used to scan a drug identification bar code that is affixed to each of the drug vials. Bar code reader 46 may comprise a fixed scanner that is positioned adjacent each drug vial 22', or alternatively, may comprise a hand-held wand that includes an optical scanner (not shown), which is moved to the drug vial to read the bar code. Controller 32 stores a table listing specific drugs commonly delivered to a patient by the multi-channel drug delivery system and their PK model data, so that once the bar code on a drug vial has been scanned, controller 32 can determine whether the drug has been recognized as one of those for which data are stored. If not, the user is directed with a message on EL display 36 to re-scan the bar code or to indicate that the drug being administered is not amongst those stored in memory. If PK control data are not stored for a drug, that drug cannot be administered under the PK model control in the preferred embodiment; however, it is contemplated that the required data might then be entered by the user on the touch screen or key pad.

A serial interface 54 is electrically coupled to controller 32, enabling the host controller to be connected to an external computer, perhaps at a remote site, through an RS-232 serial data link 52. RS-232 data link 52 can convey data bidirectionally between the external computer and controller 32, enabling, for example, the drug delivery history for a patient to be downloaded to the external computer, or addition drug PK data to be uploaded and stored in the memory of controller 32. A parallel port 58 is also provided in the preferred embodiment to convey output to a printer 56 that is coupled to the parallel port. This output can include a patient drug infusion history showing (selectively in graphical or textual format) the drug concentration over time for each drug infused into the patient during the patient case history, and predicted drug concentrations at future times.

Host controller 10 is supplied electrical power from a generally conventional system power supply with a battery backup 60. Although not separately shown, each of the components of the multi-channel drug delivery system, including those components on host controller 10, are connected to the system power supply. In the event that AC line power is disconnected, the battery backup provided with the supply will continue to operate the host controller and multi-channel drug delivery system for an extended period of time.

Figure 2:
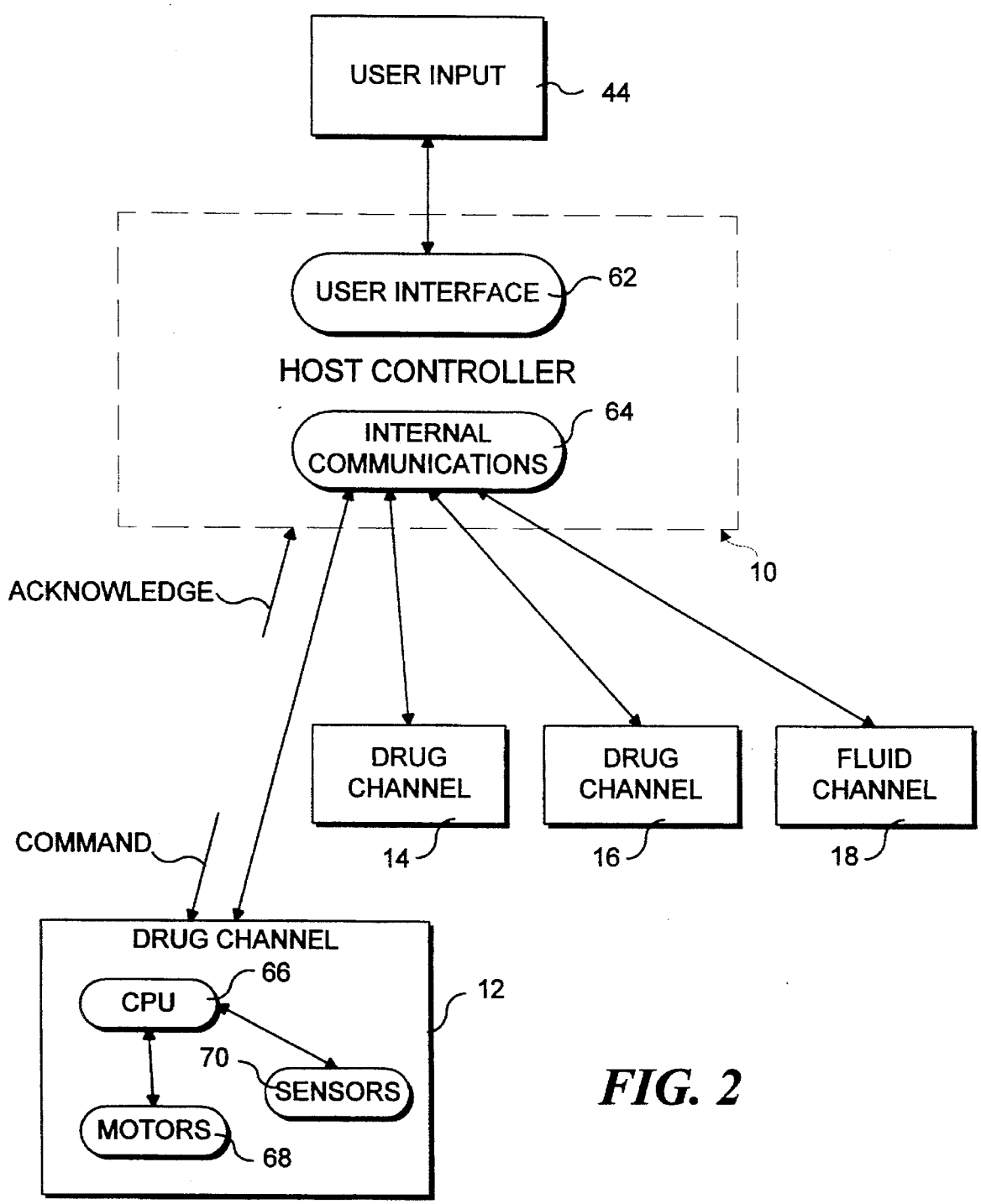
FIG. 2 is a schematic block diagram showing the relationship between the host controller and the channels of the multi-channel drug delivery system of FIG. 1, and illustrating in an exemplary fashion, the principal components of one drug delivery channel.

Turning now to FIG. 2, a block diagram shows the relationship between the user input to the system and the control of each of the plurality of drug channels that is handled by host controller 10. Selections made through user input of the operating modes and entry of the control parameters are accepted by host controller 10 through a user interface 62, which comprises the touch screen, front panel controls, and keypad. Signals developed by user interface 62 are employed by host controller 10 to control each of drug channels 12–16, and fluid channel 18. In controlling each of the drug channels, host controller 10 produces commands that are transmitted to a separate CPU 66 that is disposed within each drug channel. All three of the drug channels are identical in construction. Accordingly, the internal components of drug channel 12 shown within FIG. 2 are exemplary of those in the other two drug channels.

CPU 66 handles details of the actual operation of the cassette pump in the drug channel, under the control of host controller 10. For example, when host controller 10 causes drug channel 12 to begin infusing a drug, CPU 66 responds to the command signal from the host controller by transmitting a signal that causes motors 68 to be activated, infusing the drug at the nominal rate commanded by the host controller. In addition, each drug channel includes a plurality of sensors 70 that monitor the operation of the cassette pump, producing data signals and alarm signals that are transmitted back to the internal communications block within the host controller. These data indicate the actual rate at which a drug is being delivered through the drug channel, which is of interest in the present invention, since the actual rate of drug delivery is used in the PK model. While certain of the other signals supplied to host controller 10 by the drug channels, such as the alarm conditions, are important for safe operation of the multi-channel drug delivery system, they have little relationship to the present invention. Accordingly, these other aspects of the multi-channel drug delivery system are not further discussed.

As noted above, host controller 10 is able to selectively operate the multi-channel drug delivery system to deliver drugs in different modes. Delivery of drugs at a predefined rate and volume, and delivery of a bolus dose are generally conventional. However, host controller 10 is also able to deliver drugs through a plurality of drug channels in accordance with a PK model. The PK model can selectively control the rate of drug delivery to achieve either a desired blood plasma drug concentration of the drug within a patient's body, or a desired effect compartment drug concentration for the drug.

Figure 3:
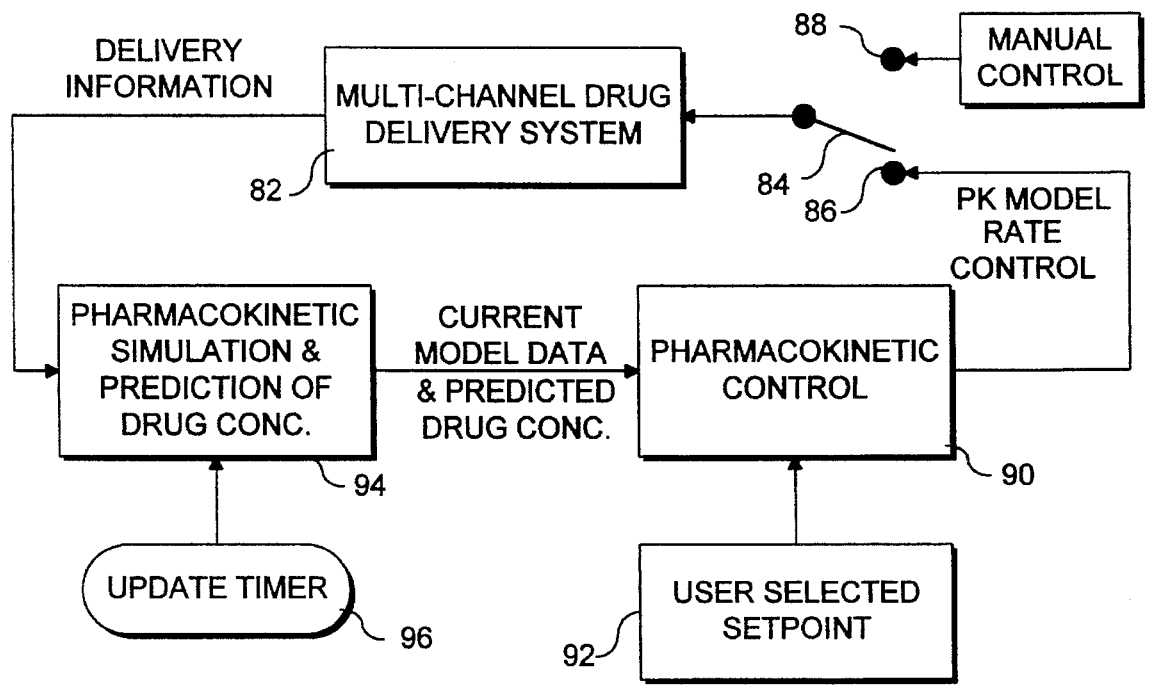
FIG. 3 is a schematic block diagram illustrating the use of a PK model for controlling the multi-channel drug delivery system of FIG. 1.

A functional block diagram of the PK model used by host controller 10 in controlling the multi-channel drug delivery system is shown in FIG. 3. In this FIGURE, a block 82 represents the multi-channel drug delivery system that is controlled by the model. The user has the option of selecting either to control drug delivery in accordance with the PK model, or alternatively, to administer a drug manually, either as a bolus dose or as a continuous infusion at a defined rate. It is important to note that control of the drug delivery rate in accordance with the PK model can be interrupted at any time, should the user switch to the manual control to deliver a bolus dose or to provide a defined rate of continuous drug infusion. Delivery under the control of the PK model can then be selectively resumed. This user selective option for controlling the infusion of drugs is represented by a switch 84 in FIG. 3. In a position 88, switch 84 selects the infusion of drugs in accordance with manual control, and in a position 86, the switch selects the infusion of drugs in accordance with the PK model.

Assuming that switch 84 has been selectively set by the user to administer drugs in accordance with the PK model, the program executing on controller 32 (shown in FIG. 1) transmits control signals to the multi-channel drug delivery system in block 82 that set the rate of drag delivery to achieve either the desired blood plasma drug concentration selected by the user, or the desired effect compartment drug concentration. The source of these control signals is represented in FIG. 3 by a block 90. As shown in the Figure, a block 92 provides the user input to the PK control in block 90 corresponding to a selected setpoint. Controller 32 on host controller 10 executes the PK simulation in a block 94 to determine current model data and the predicted drug concentration (blood plasma and/or effect compartment) that are periodically supplied to the PK control in block 90. Either type of drug concentration setpoint can be changed at any time and the PK model will control the administration of the drug to achieve the new setpoint. An update timer 96 establishes the time interval at which the current model data and predicted drug concentration are transferred from the PK simulation in block 94 to the PK control in block 90. In the preferred embodiment, update timer (which is implemented by controller 32) triggers an update at intervals of five seconds.

The PK simulation in block 94 that is used in the preferred embodiment models the blood plasma drug concentration and/or effect compartment drug concentration of the drug being administered based upon variables that depend upon the specific drug being infused, and patient specific data such as the weight, the age, and gender of the patient. Another important variable is the actual rate at which the multi-channel drug delivery system is infusing the drug. The rate of delivery of the drug is supplied by the multi-channel drug delivery system in block 82 to the PK simulation in block 94. This feedback signal, which indicates the actual delivery rate of the drug, allows the PK model to compensate for an imperfect pump response to a requested change in the rate of drug delivery, and to compensate for alarm caused delays, and other interruptions in the delivery of the drug to a patient. The actual delivery rate also enables a more accurate drug concentration prediction to be achieved, since the cassette pump may not deliver a drug at the rate it was commanded to by the PK model control. Furthermore, when the user selectively operates the multi-channel drug delivery system under manual control, the PK simulation uses the drug rate delivery information to continue to track and predict the drug concentration (either or both blood plasma and effect compartment), even though it is not controlling that rate. This feature enables the predicted rate and historical rate to be displayed to the user for each drug administered, at any time, including during manual control of drug delivery and after the delivery of a drug is interrupted or even terminated.

Effect Compartment PK Model

Figure 4:
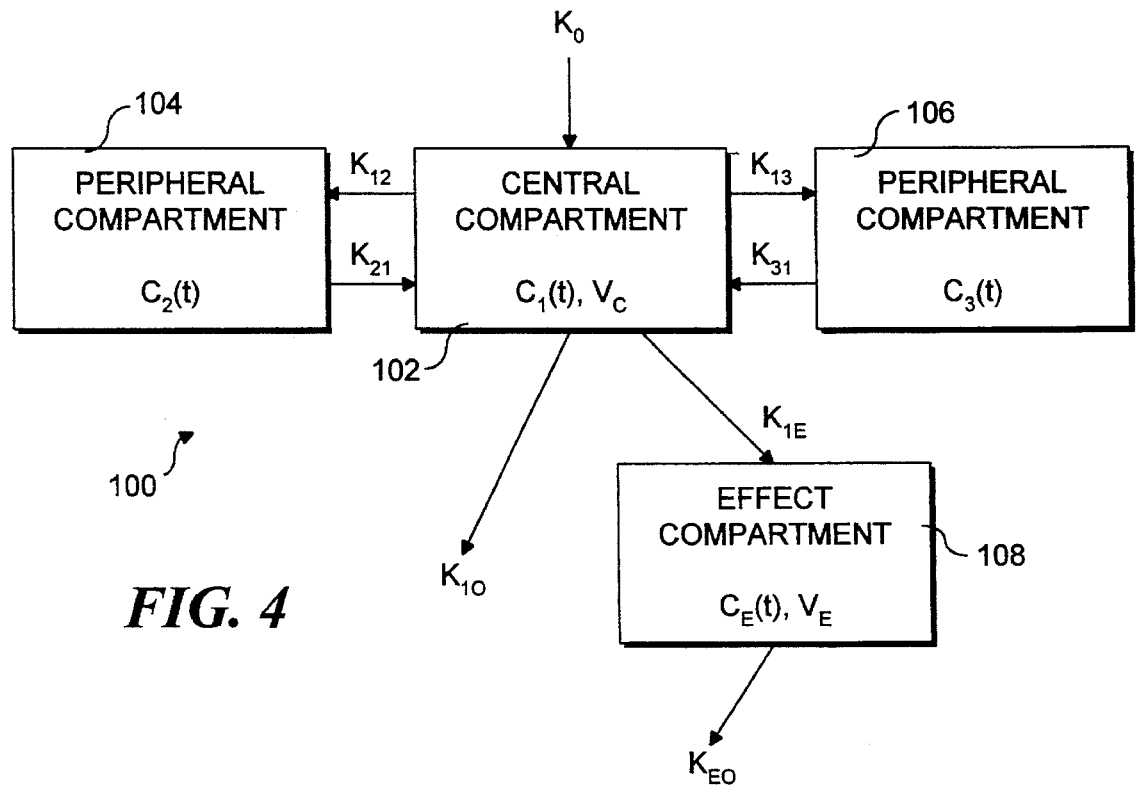
FIG. 4 is a schematic diagram showing an effect compartment model used in the preferred embodiment of the present invention.

FIG. 4 illustrates an effect compartment PK model 100 that is used in the preferred embodiment by the PK simulation to predict the blood plasma drug concentration and the effect compartment drug concentration of the drug in the patient. Although other PK models could be used with the present invention, it will be helpful to explain this model so that the reader can understand how the effect compartment drug concentration level is used. PK model 100 employs a central compartment 102 and two peripheral compartments 104 and 106. The actual physiological components of the patient's body to which each of these compartments corresponds generally depend upon the type of drug being infused, the characteristics of the drug, and the manner of the infusion. However, for many types of drugs that are infused intravascularly, central compartment 102 corresponds to the circulatory system of the patient; one of the peripheral compartments corresponds to well-perfused tissue; and the other compartment corresponds to poorly-perfused tissue. The rate of infusion or delivery of the drug into central compartment 102 is defined by the variable $K_0$. The drug moves bidirectionally between central compartment 102 and peripheral compartment 104 with rate constants $K_{12}$ and $K_{21}$. Similarly, the drug moves bidirectionally between central compartment 102 and peripheral compartment 106 with rate constants $K_{13}$ and $K_{31}$. The drug also moves into an effect compartment 108 at a rate $K_{1E}$. In this model, the drug irreversibly clears the effect compartment at a rate $K_{EO}$ and irreversibly clears the central compartment at a rate $K_{10}$. Use of effect compartment 108 in this PK model is helpful in achieving optimal drug delivery control, since the effect compartment model more accurately represents the time course of some drug effects than does the time course of the drug concentration within the central compartment. The differences between the two types of PK modeling control are referred to as "kinetic-dynamic dissociation."

As will be shown below, as a function of time, the rate constant $K_{1E}$ is directly proportional to the effect compartment clearance rate, $K_{EO}$. Furthermore, the rate constant $K_{1E}$ is much smaller than the rate constants in the rest of the model. The volume of effect compartment 108 and the relative mass of the drug within it compared to the other compartments of the model is assumed to be so small as to have little effect on the pharmacokinetics of the central compartment. Based upon this assumption, the mass transfer of the drug between the central compartment and the two peripheral compartments can still be described by the equations conventionally used for the three compartment model.

Mathematical Development of PK Model

While the present invention is not limited to use of the PK model employed in the preferred embodiment, it is helpful to understand how that model predicts blood plasma drug concentration and effect compartment drug concentration for use in controlling the rate of drug delivery. The following theoretical explanation explains how the three compartment model used for predicting and controlling blood plasma drug concentration is modified for use in predicting and controlling with the effect compartment model.

In the three compartment PK model, the plasma drug concentrations in the respective compartments 102, 104, and 106 are represented by $C_i(t)$, for i=1 through 3, expressed in μg/l, and the volume of central compartment 102 is represented by $V_c$, expressed in l/kg. The drug is infused into the central compartment at a rate $K_0(t)$, expressed in μg/kg/min., as are all other rate constants. The rate at which the concentration changes or the mass transfer of the drug into (and out of) the three compartments over time, t, is defined by the following three equations:

$$\frac{dC_1(t)}{dt} = \frac{K_0(t)}{V_C} - (K_{10} + K_{12} + K_{13})C_1(t) + K_{21}C_2(t) + K_{31}C_3(t) \quad (1)$$

$$\frac{dC_2(t)}{dt} = K_{12}C_1(t) - K_{21}C_2(t) \quad (2)$$

$$\frac{dC_3(t)}{dt} = K_{13}C_1(t) - K_{31}C_3(t) \quad (3)$$

Taking the Laplace transform of Equations 1–3 and solving for the drug concentration in central compartment 102 yields the following relationship:

$$\mathcal{C}_1(s) = \frac{\mathcal{X}_0(s)V_C^{-1}(s+K_{21})(s+K_{31}) + C_1^0 s^2 + [C_1^0(K_{21}+K_{31}) + C_2^0 K_{21} + C_3^0 K_{31}]s + (C_1^0 + C_2^0 + C_3^0)K_{21}K_{31}}{s^3 + a_1 s^2 + a_3} \quad (4)$$

where $\mathcal{C}_1(s)$ is the Laplace transform of the concentration time function $C_1(t)$ of the central compartment, the $C_i^0$ represent the initial concentration of the drug in the ith compartment, and where:

$$a_1 = K_{10} + K_{12} + K_{21} + K_{13} + K_{31} \quad (5)$$

$$a_2 = K_{31}K_{21} + K_{10}K_{31} + K_{12}K_{31} + K_{10}K_{21} + K_{13}K_{21} \quad (6)$$

$$a_3 = K_{10}K_{21}K_{31} \quad (7)$$

Based upon Equation 4, the initial plasma drug concentration for all three compartments are required to predict the subsequent central compartment drug concentration; however, the model begins predicting the central compartment drug concentration at a time zero, when the drug concentration in the three compartments is assumed to be zero. All further development of this PK model is based upon that assumption.

In view of that assumption, Equation 4 can thus be simplified and the impulse response function (or unit disposition function) for the central compartment can be derived as follows:

$$\mathcal{U}_1(s) = \frac{\mathcal{C}_1(s)}{\mathcal{X}_0(s)} = \frac{V_C^{-1}(s+K_{21})(s+K_{31})}{(s^3 + a_1 s^2 + a_2 s + a_3)} = \frac{\mathcal{P}(s)}{\mathcal{Q}(s)} \quad (8)$$

The denominator of Equation 8 can be factored into the form:

$$\mathcal{Q}(s) = (s - \lambda_0)(s - \lambda_1)(s - \lambda_2) \quad (9)$$

where $\lambda_0$, $\lambda_1$, and $\lambda_2$ are the three roots of the cubic equation, $\mathcal{Q}(s) = 0$, and can be determined from the following three relationships:

$$\lambda_0 = m \cos\left(\frac{\theta}{3}\right) - \frac{a_1}{3} \quad (10)$$

$$\lambda_1 = m \cos\left(\frac{\theta}{3} + \frac{2\pi}{3}\right) - \frac{a_1}{3} \quad (11)$$

$$\lambda_2 = m \cos\left(\frac{\theta}{3} + \frac{4\pi}{3}\right) - \frac{a_1}{3} \quad (12)$$

The values for m and $\theta$ in the preceding three equations are defined as follows:

$$\theta = \cos^{-1}\left(\frac{\frac{2a_1^3}{27} - \frac{a_1 a_2}{3} + a_3}{2\sqrt{\frac{-\left(a_2 - \frac{a_1^2}{3}\right)^3}{27}}}\right) \quad (13)$$

$$m = 2\sqrt[3]{\left(\frac{-\left(a_2 - \frac{a_1^2}{3}\right)^3}{27}\right)^{\frac{1}{2}}} \quad (14)$$

Given the values of the $\lambda_i$'s from Equations 10, 11, and 12, the time domain impulse response function for central compartment 102 can be determined by taking the inverse Laplace transform of Equation 8. The time domain response for the central compartment drug concentration can then be determined by taking the inverse Laplace transform of $\mathcal{C}_1(s)$ from Equation 4 with the relationship from Equation 8. Substituting the time domain impulse response into the time domain response for the central compartment drug concentration yields:

$$C_1(t) = \int_0^t K_0(\tau) \sum_{i=0}^{2} A_i e^{\lambda_i(t-\tau)} d\tau = \quad (15)$$

$$\sum_{i=0}^{2} A_i \int_0^t K_0(\tau) e^{\lambda_i(t-\tau)} d\tau = \sum_{i=0}^{2} C_{1i}(t)$$

where the partial sums $C_{1i}(t)$ are defined by:

$$C_{1i}(t) = A_i \int_0^t K_0(\tau) e^{\lambda_i(t-\tau)} d\tau = A_i e^{\lambda_i t} \int_0^t K_0(\tau) e^{-\lambda_i \tau} d\tau \quad (16)$$

The values for $V_c$ and the rate constants $K_{ij}$ are generally determined by a nonlinear least squares analysis of plasma level vs. time data and are available for many drugs in the published literature, for storage in the memory on controller 32 (FIG. 1). Given these PK parameters, the values for the $A_i$'s and $\lambda_i$'s can be determined, enabling the plasma drug concentration to be predicted at any time, past, present, or future, so long as the actual infusion rate, $K_0(t)$ is supplied to the controller by the multi-channel drug delivery system.

Although Equations 14 and 15 provide an analytical model that can track and predict the blood plasma drug concentrations over time, in controller 32, it is not practical to store the entire continuous drug infusion rate history of $K_0(t)$. A solution more suitable for real-time control of the multi-channel system is based upon a simplification of the foregoing theoretical solution. Instead of storing a continuous infusion rate history, controller 32 only evaluates the model at discrete time intervals, t=nT, determined by update timer 96 (FIG. 3). This interval is chosen to be relatively short (e.g., 5 seconds) so that the drug infusion rate will be substantially constant over the time interval. Thus, $K_0(t) = K_n$ for $(n+1)T > t \geq nT$. Equation 16 can then be expressed as:

$$C_{1i}(nT) = e^{\lambda_i T} C_{1i}((n-1)T) - \frac{A_i K_n}{\lambda_i}[1 - e^{\lambda_i T}] \quad (17)$$

To simplify Equation 17, the variables $\alpha_i = e^{\lambda_i T}$ and $\beta_i =$ $$\beta_i = \frac{-A_i[1 - \alpha_i]}{\lambda_i},$$

for i=0 through 2 are substituted, enabling Equation 17 to be expressed as:

$$C_{1i}(nT) = \alpha_i C_{1i}((n-1)T) + \beta_i K_n \quad (18)$$

Since the $A_i$'s and $\lambda_i$'s are constants for a given PK model that has a fixed time interval T between simulations, the parameters $\alpha_i$'s and $\beta_i$'s are constants that can be predetermined and the estimated blood plasma drug concentration can readily be determined at each discrete time interval by using Equation 18.

The next step is to employ the PK simulation used to determine estimates of the blood plasma drug concentration at any point in time after the drug infusion is initiated to control the rate of drug delivery by the multi-channel drug delivery system. The PK model can be used for each of the drugs administered, or different PK simulations can be used for each drug. If the user selects a blood plasma drug concentration setpoint S and if $R_n$ is the theoretical infusion rate between a time nT and a time t=(n+1)T, the relationship between S and $R_n$ can be derived from Equations 15 and 18, as follows:

$$S = C_1((n+1)T) = \sum_{i=0}^{2} [\alpha_i C_{1i}(nT) + \beta_i R_n] = \quad (19)$$

$$\sum_{i=0}^{2} [\alpha_i C_{1i}(nT)] + R_n \sum_{i=0}^{2} \beta_i$$

and solving for $R_n$:

$$R_n = \frac{S - \sum_{i=0}^{2} [\alpha_i C_{1i}(nT)]}{\sum_{i=0}^{2} \beta_i} \quad (20)$$

The denominator in Equation 20 is a constant and the second term in the numerator is the predicted plasma drug concentration, assuming that there is no drug infusion from the current time until the next update time. The infusion rate is the theoretical rate. Since controller 32 can only cause the multi-channel drug delivery system to operate within its design parameters, it may not be possible to achieve the theoretical rate. The delivery rate for cassette pumps 20 in the preferred embodiment are limited to the range 0.1 ml/hr to 1200 ml/hr, and the appropriate extreme value of this actual range is used in the event that the calculated delivery rate for a drug or combination of drugs is outside the cassette pump design limits.

The three compartment PK model discussed above is readily extended to the effect compartment model shown in FIG. 4, because the mass of the drug within the effect compartment is so small compared to the other compartments. A time rate of change of the effect compartment drug concentration is defined by the following:

$$\frac{dC_E(t)}{dt} = K_{1E} C_1(t) - K_{EO} C_E(t) \quad (21)$$

It will be apparent that as the drug delivery continues over a long period of time, the effect compartment drug concentration will cease changing and achieve a steady-state value. When that condition occurs, the following relationship will exist:

$$C_E(\text{steady} - \text{state}) - \frac{K_{1E}}{K_{EO}} C_1(\text{steady} - \text{state}) \quad (22)$$

From Equation 22, it will be apparent that under steady-state conditions, the effect compartment drug concentration level is directly proportional to the central compartment drug concentration level. Although the effect compartment is a purely hypothetical construct, it has been clinically determined that the drug effect is usually related to the plasma drug concentration. Accordingly, it can be assumed that the effect compartment drug concentration level equals the central compartment drug concentration at steady state, and therefore, that $K_{1E}=K_{EO}$.

Taking the Laplace transform of Equation 21 yields the following in the frequency domain:

$$s\mathcal{C}_E(s) = K_{EO}\mathcal{C}_1(s) - K_{EO}\mathcal{C}_E(s) \quad (23)$$

From Equations 8, 9, and 23, the Laplace transform of the central compartment drug concentration can be derived, where $\lambda_3 = -K_{EO}$, yielding:

$$\mathcal{C}_E(s) = \frac{K_{EO}\mathcal{C}_1(s)}{s + K_{EO}} = \frac{\lambda_3}{(s-\lambda_3)} \frac{\mathcal{X}_0(s)\mathcal{P}(s)}{\mathcal{Q}(s)} = \quad (24)$$

$$\frac{\lambda_3 \mathcal{X}_0(s)\mathcal{P}(s)}{\prod_{i=0}^{3}(s-\lambda_i)}$$

Using the same technique that was applied in deriving the central compartment impulse response, the impulse response function for the effect compartment can be expressed as:

$$\mathcal{U}_E(t) = \mathcal{L}^{-1}\left[\frac{\mathcal{C}_E(s)}{\mathcal{X}_0(s)}\right] = \mathcal{L}^{-1}\left[\frac{\lambda_3 \mathcal{P}(s)}{\prod_{i=0}^{3}(s-\lambda_i)}\right] = \quad (25)$$

$$\sum_{i=0}^{3}[B_i e^{\lambda_i t}]$$

where the parameter $B_i$ is used to simplify the expression and is equal to:

$$B_i = \left[\frac{\lambda_3 \mathcal{P}(s)}{\frac{d}{ds}\left[\prod_{j=0}^{3}(s-\lambda_j)\right]}\right]^{s=\lambda_i} \text{ for } i = 0 \text{ through } 3 \quad (26)$$

The time domain response for the effect compartment concentration can then be determined from the inverse Laplace transformation of $C_E(s)$ using Equation 24 as follows:

$$C_E(t) = \mathcal{L}^{-1}\{\mathcal{C}_E(s)\} = \mathcal{L}^{-1}\{\mathcal{X}_0(s)\mathcal{U}_E(s)\} = \quad (27)$$

$$\int_0^t K_0(\tau)\mathcal{U}_E(t-\tau)d\tau =$$

$$\sum_{i=0}^{3}\left[B_i \int_0^t K_0(\tau)e^{\lambda_i(t-\tau)}\right]d\tau = \sum_{i=0}^{3} C_{Ei}(t)$$

where the partial sums $C_{Ei}(t)$ are defined as:

$$C_{Ei} = B_i \int_0^t K_0(\tau)e^{\lambda_i(t-\tau)}d\tau = B_i e^{\lambda_i t}\int_0^t K_0(\tau)e^{-\lambda_i \tau}d\tau \quad (28)$$

Applying much the same approach as discussed above for deriving the central compartment concentration simulation model, a recursive solution can easily be derived. Assuming that the drug infusion rate is constant over each discrete period T, Equation 28 can be simplified to obtain the following expression:

$$C_{Ei}(nT) = \alpha_i C_{Ei}((n-1)T) + \gamma_i K_n \quad (29)$$

where the $\alpha_i$'s are defined above and $$\gamma_i = \frac{-B_i[1-\alpha_i]}{\lambda_i}$$

for i=0 through 3. For a given PK model and fixed interval T, the $B_i$'s, $\lambda_i$'s, $\alpha_i$'s, and $\gamma_i$'s are all constants and can be predetermined and stored in ROM on controller 32. Using Equations 27 and 29, controller 32 can model the effect compartment drug concentration level at any time after the PK model begins the drug delivery to determine a predicted level based upon a defined delivery rate, and can readily control the delivery rate to achieve a desired effect compartment drug concentration setpoint that is entered by the user.

Predicting and Controlling Drug Concentration Levels

The steps involved in controlling the delivery of a drug to a patient by the multi-channel drug delivery system in accordance with a PK model can logically be divided into two procedures. In the first procedure, which is shown as a series of blocks comprising a flow chart in FIG. 5, predicted drug concentrations within the effect compartment and within the blood plasma are determined. This procedure runs for each drug administered by the multi-channel drug delivery system, throughout the entire patient case, including during interruptions and after termination of drug delivery. The same procedure can be used with a single drug channel delivery system. Different PK models can selectively be used for modeling the predicted drug concentration of each drug.

Figure 6:
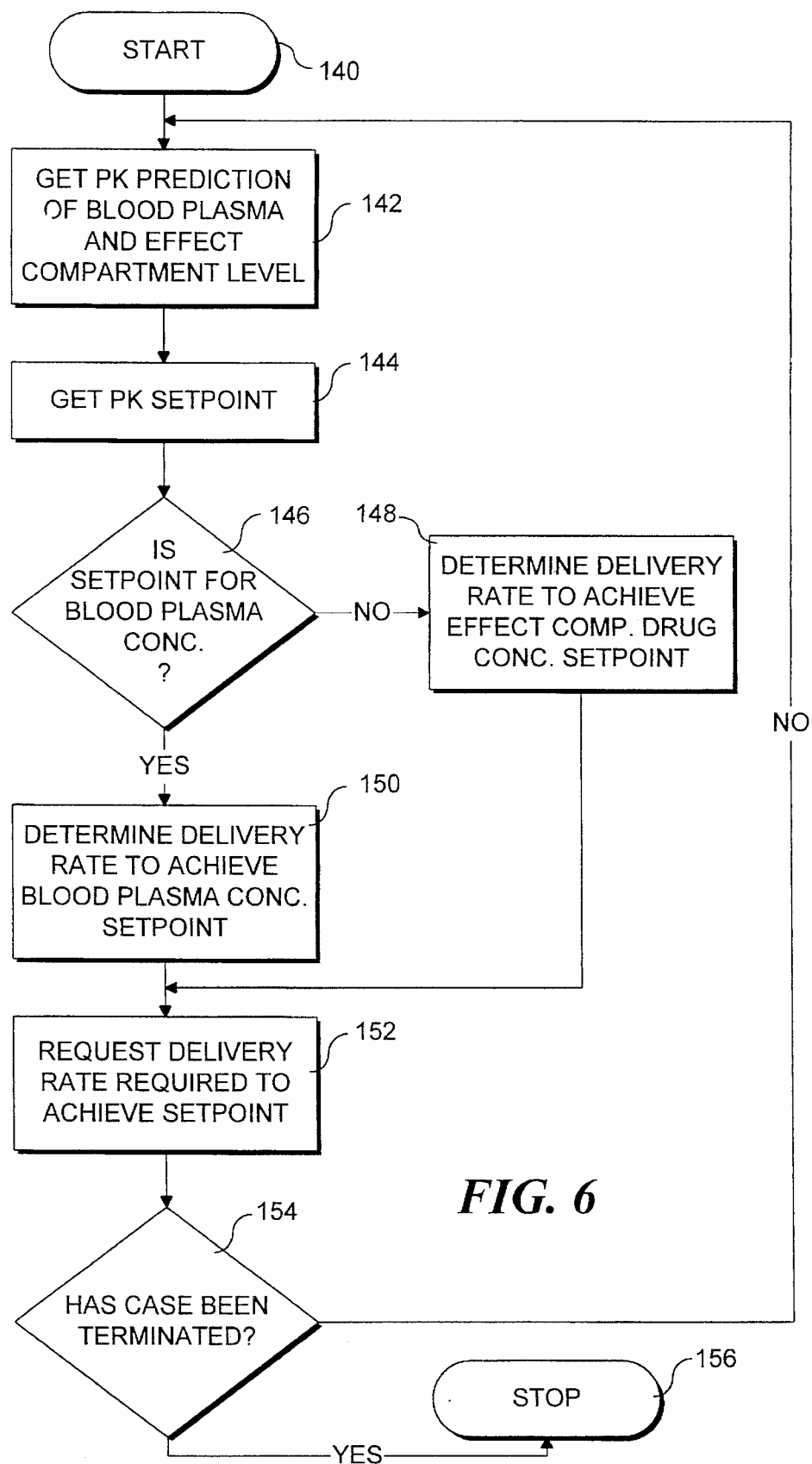
FIG. 6 is a flow chart showing the logical steps employed by the PK model in controlling the rate at which a drug is delivered to a patient to achieve either a desired blood plasma drug concentration setpoint or to achieve a desired effect compartment drug concentration setpoint.

In the second procedure, which is illustrated by the flow chart of FIG. 6, the delivery rate is determined and controlled to achieve the user specified drug concentration setpoint. The procedure of FIG. 6 is applied to each of a plurality of drugs delivered under the PK model control mode, thereby achieving a desired drug concentration setpoint for the drugs, but can be used for controlling a single channel drug delivery system in a similar manner. The controller tracks the drug concentration in maintaining the PK prediction model over time, regardless of the drug channel through which the drug is being administered, and regardless of whether the administration of the drug is interrupted or terminated.

Figure 5:
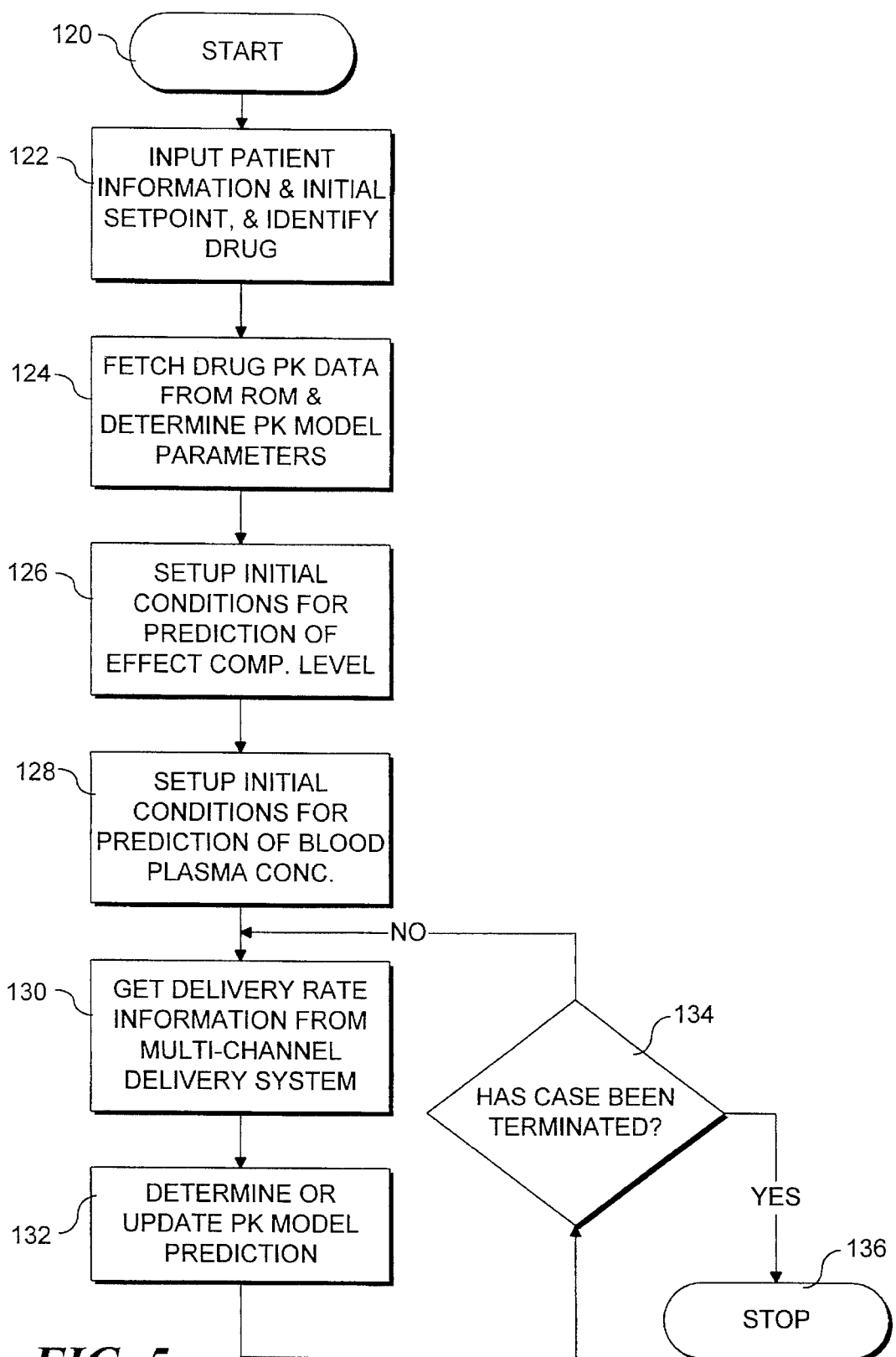
FIG. 5 is a flow chart showing the steps for using the PK model to predict drug concentration levels.

Turning first to FIG. 5, the steps involved in predicting the drug concentration begin with a start block 120. A block 122 provides for input by the user of patient information, including as required, the patient's weight, age, and gender. Input of these data start the PK prediction model running. In addition, the user enters the (initial) desired drug concentration setpoint, either for blood plasma drug concentration or effect compartment drug concentration. Then, the user scans the drug vial, so that controller 32 (FIG. 1) can identify the drug being delivered to the patient. Identification of the drug is important, since, as noted in a block 124, the controller must fetch the drug PK data that are stored in memory in order to properly determine the PK model parameters that will be used.

Table 1 lists PK model data for the drug propofol, which were derived from "Seminars in Anesthesia 11" by Dyck and Sharer (Supp. 11):2–4, 1992.

In blocks 126 and 128, the controller sets tip the initial conditions for prediction of the drug concentration levels. As noted in the above mathematical discussion of the PK model, it is assumed that the model begins with zero drug concentration in each of the central and peripheral compartments, and in the effect compartment.

Since the actual delivery rate of the drug may not correspond to the delivery rate requested, a block 130 enables the controller to obtain the actual delivery rate information from the multi-channel drug delivery system. In addition to the advantages already enumerated above, this step compensates for the fact that the drug delivery rate cannot be controlled in an instantaneous step-wise function; a time delay inherently exists between a request to change the drug delivery rate and the pumping mechanism's ability to satisfy that delivery rate.

In a block 132, the controller uses the data provided to it to initially determine, and thereafter to subsequently update, the PK model prediction of effect compartment drug concentration and/or blood plasma drug concentration. A decision block 134 then determines if the current patient case has been terminated. It should be again emphasized that delivery of the drug in accordance with the PK model can be interrupted at any time for delivery of a bolus dose or of a manually set continuous infusion without terminating the prediction PK model. During any interruption of the drug delivery, prediction of the drug concentration continues in accordance with the steps of FIG. 5 so that the PK model drug concentration level for any drug can be displayed and so that control by the PK model can be initiated or resumed at a later time. The controller will thus continue to selectively show the predicted drug concentrations of any of the drugs administered during the patient case, after delivery of the drug is terminated.

If the patient case is actually terminated in decision block 134, the logic proceeds to a stop block 136. Otherwise, the logic continues to reiteratively proceed through blocks 130 and 132, continuously updating the PK model prediction of drug concentration in the blood plasma and/or within the effect compartment of the patient.

Turning now to FIG. 6, control of the drug delivery in accordance with the PK model is implemented beginning

TABLE 1

PK MODEL PARAMETERS FOR PROPOFOL

| Variable | Formula | Units | Description |
| --- | --- | --- | --- |
| $V_c$ | $9.64 - 0.0512*age$ | liter | Central Comp. Volume |
| $K_{10}$ | $(0.652 + 0.0148*weight)/V_1$ | $minute^{-1}$ | Central Comp. Clearance |
| $K_{12}$ | $1.68/V_1$ | $minute^{-1}$ | Rate Constant from Central Comp. to Periph. Comp. |
| $K_{21}$ | $1.68/19.4$ | $minute^{-1}$ | Rate Constant from Periph. Comp. to Central Comp. |
| $K_{13}$ | $(2.67 - 0.0145*age)/V_1$ | $minute^{-1}$ | Rate Constant from Central Comp. to Periph. Comp. |
| $K_{31}$ | $(2.67 - 0.0145*age)/(571 - 1.66*age)$ | $minute^{-1}$ | Rate Constant from Periph. Comp. to Central Comp. |
| $K_{EO}$ | $0.693/1.1$ | $minute^{-1}$ | Effect Comp. Clearance |

In Table 1, the formulae for determining each of the parameters are dependent upon the age and weight of the patient. Each drug commonly administered by the multi-channel drug delivery system will have its own set of data stored in ROM. These data are used for determining the PK model parameters, once the patient's data have been entered by the user.

with a start block 140. A block 142 obtains the PK prediction of blood plasma and effect compartment level, determined as described above. In a block 144, the controller obtains the current PK setpoint. This setpoint will either be the initial setpoint that was previously entered by the user in FIG. 5 or a subsequent setpoint. At any time, the user can change the desired drug concentration setpoint, and the PK model will adjust the rate of drug delivery to achieve the new setpoint as quickly as possible.

A decision block 146 determines if the setpoint defines the blood plasma drug concentration, or alternatively, the effect compartment drug level desired by the user. If the setpoint does not define a desired blood plasma concentration, the setpoint must logically define the desired effect compartment drug concentration. If so, a block 148 determines the delivery rate necessary to achieve the effect compartment drug concentration entered by the user as a setpoint. Otherwise, the logic proceeds to a block 150, in which the controller determines the delivery rate that will be necessary to achieve the blood plasma drug concentration setpoint entered by the user. The steps carried out in either block 148 or block 150 are accomplished as described above. The controller then requests the multi-channel delivery system to set a delivery rate that was just determined in a block 152.

A decision block 154 determines if the patient case has been terminated. The decision that is made here corresponds to that discussed above in connection with FIG. 5. A positive response to decision block 154 leads to a stop block 156. Otherwise, the logic loops back to block 142 to get the next PK prediction of blood plasma and effect compartment drug concentration, which is provided in the preferred embodiment at five second intervals.

While the disclosure of the preferred embodiment has discussed details of a specific PK model, it should be recognized that the present invention is not in any way limited to that model. It should also be apparent that different PK models can be implemented in controlling each of the plurality of drug channels of the multi-channel drug delivery system. One or more drug channels can be controlled to deliver a bolus or continuous infusion (manual control) while one or more other drug channels are delivering drugs in accordance with the same or different PK models. Considerable versatility is thus provided to the physician in administering various types of drugs to a patient. By using a PK model to control drug delivery rate in each drug channel, the physician can quickly achieve the desired medicinal effect on the patient, without the need to compute and control the rate manually.

Since the predicted drug concentration history is maintained by controller 32, a physician can selectively display the past and current blood plasma drug concentration or the effect compartment drug concentration, or can display either predicted drug concentration at a time in the future, on the EL display of host controller 10. This information can be very helpful to a physician in evaluating the need for changes in the desired drug concentration setpoint. At any time, the physician can enter different drug concentration setpoints, causing the PK model to adapt the control of the drug delivery to achieve the new setpoint—either blood plasma or effect compartment drug concentration. Furthermore, since a continuous drug infusion history is maintained for a patient throughout the case, that history can either be printed or transmitted over the RS-232 data link to a remote computer for further processing and display.

Although the present invention has been described in connection with the preferred form of practicing it, it will be understood by those of ordinary skill in the art that many modifications can be made thereto within the scope of the claims that follow. Accordingly, it is not intended that the scope of the invention in any way be limited by the above description, but that it be determined entirely by reference to the claims that follow.

The invention in which an exclusive right is claimed is defined by the following:

1. A control for a multi-channel drug delivery system with which a plurality of drugs are selectively administered to a patient through a plurality of drug channels in accordance with a PK model, comprising:

(a) a processor that is controlled in accordance with a set of program instructions that determine the steps implemented by said PK model;

(b) a memory, coupled to the processor, said memory storing the set of program instructions and a plurality of parameters used by the PK model;

(c) a display, coupled to the processor, on which are displayed the parameters and PK model data, including a concentration of a drug within the patient as a function of time;

(d) a user interface, coupled to the processor, said user interface enabling a user to input at least some of the plurality of parameters used by the PK model in controlling administration of each drug to the patient, and including identification means for identifying the drug that is being administered in each of the drug channels; and (e) PK model prediction means, embodied in the processor executing said set of program instructions, for determining a drug concentration within the patient over time for each drug, as each drug is administered by the multi-channel drug delivery system, said PK model prediction means determining the drug concentration:

(i) during any interruption and after a termination of the drug delivery; and (ii) regardless of any change in the drug channel through which any drug is delivered.

2. The control of claim 1, wherein the processor is controlled by the program instructions to selectively model and control one of an effect compartment drug concentration of a drug in the patient, and a blood plasma drug concentration of the drug in the patient.

3. The control of claim 1, wherein the memory stores blood plasma drug concentrations over time for the plurality of drugs.

4. The control of claim 3, wherein the display selectively shows at least one of a predicted and a historical blood plasma drug concentration over time for any of the plurality of drugs.

5. The control of claim 1, wherein the memory stores effect compartment drug concentrations over time for the plurality of drugs.

6. The control of claim 5, wherein the display selectively shows at least one of a predicted and a historical effect compartment drug concentration for any of the plurality of drugs over time.

7. The control of claim 1, wherein the user interface includes a mode switch enabling the user to select between a manual mode and a PK model control mode for controlling the delivery of any of the plurality of drugs by the multi-channel drug delivery system, said PK prediction means continuing to determine and track at least one of a blood plasma drug concentration and an effect compartment drug concentration for over time while operating in the manual mode, thereby enabling the processor to control administration of a drug in the PK model control mode if said mode is selected after the manual mode was used to control delivery of the drug by the multi-channel drug delivery system.

8. The control of claim 7, wherein the display shows at least one of the blood plasma drug concentration and the effect compartment drug concentration of said drug during operation of the multi-channel drug delivery system in the manual mode.

9. The control of claim 8, wherein the display shows for said drug, at least one of a historical and a predicted blood plasma drug concentration level over time, and of a historical and a predicted effect compartment drug concentration over time, during operation of the multi-channel infusion system in the manual mode.

10. The control of claim 8, wherein the display shows for the drug, at least one of a historical and a predicted blood plasma drug concentration over time, and of a historical and a predicted effect compartment drug concentration over time:
   (a) after delivery of the drug is terminated; or
   (b) after a different drug is delivered in the same drug channel as said drug, and then delivery of said drug is resumed in said drug channel; or
   (c) after delivery of the drug is resumed in a different drug channel.

11. A control for a multi-channel drug delivery system with which any of a plurality of drugs are selectively administered to a patient through a plurality of drug channels in accordance with a PK model, comprising:
   (a) a processor that is controlled in accordance with a set of program instructions that determine the steps of said PK model;
   (b) a memory, coupled to the processor, said memory storing the set of program instructions and a plurality of parameters used in the PK model;
   (c) a display, coupled to the processor, on which are displayed the parameters and data indicative of a state of the PK model; and
   (d) a user interface, coupled to the processor, said user interface enabling a user to input at least some of the plurality of parameters used by the PK model in controlling administration of a drug to the patient and including a selector switch that selectively determines whether the control uses the PK model to achieve either:
      (i) a desired blood plasma drug concentration; or
      (ii) a desired effect compartment drug concentration.

12. The control of claim 11, wherein the memory stores blood plasma drug concentrations over time for the plurality of drugs.

13. The control of claim 12, wherein the display is controlled by the processor to selectively display at least one of a predicted and a historical blood plasma drug concentration.

14. The control of claim 11, wherein the memory stores effect compartment drug concentrations over time.

15. The control of claim 14, wherein the display selectively shows at least one of a predicted and a historical effect compartment drug concentration over time.

16. The control of claim 11, wherein the user interface includes a mode switch enabling the user to select between a manual mode and a PK model control mode for controlling the multi-channel drug delivery system, said processor continuing to model and track at least one of a blood plasma drug concentration and an effect compartment drug concentration for the plurality of drugs over time while operating in the manual mode, thereby enabling the processor to control administration of any drug in the PK model control mode if said mode is selected after the manual mode was used to control delivery of the drug.

17. The control of claim 16, wherein the processor causes the display to show at least one of the blood plasma drug concentration and the effect compartment drug concentration of a drug during operation of the multi-channel drug delivery system to deliver the drug in the manual mode.

18. The control of claim 17, wherein the display shows at least one of a historical and a predicted blood plasma drug concentration level for the drug over time, and of a historical and a predicted effect compartment drug concentration for the drug over time, during operation of the multi-channel infusion system to delivery the drug in the manual mode.

19. The control of claim 17, wherein the display shows at least one of a historical and a predicted blood plasma drug concentration level over time, and of a historical and a predicted effect compartment drug concentration over time, after delivery of the drug is terminated.

20. The control of claim 11, wherein the user interface includes means for selectively determining the PK model used for each of the plurality of drugs, enabling the user to select a different PK model for different drugs.

21. The control of claim 11, wherein the user interface includes means for identifying the drug channel through which a specific drug is being delivered, enabling the PK model to control the delivery of said specific drug regardless of any change in the drug delivery channel through which it is delivered.

22. A control for a drug delivery system with which a drug is selectively administered to a patient in accordance with a PK model, comprising:
   (a) a processor that is controlled in accordance with a set of program instructions that determine the steps of said PK model;
   (b) a memory, coupled to the processor, said memory storing the set of program instructions and a plurality of parameters used in the PK model;
   (c) a display, coupled to the processor, on which are displayed the parameters and data indicative of a state of the PK model; and
   (d) a user interface, coupled to the processor, said user interface enabling a user to input at least some of the plurality of parameters used by the PK model in controlling administration of the drug to the patient and including a selector switch that selectively determines whether the control uses the PK model to achieve:
      (i) a desired blood plasma drug concentration; or
      (ii) a desired effect compartment drug concentration.

23. The control of claim 22, wherein the memory stores blood plasma drug concentrations over time for the drug.

24. The control of claim 23, wherein the display selectively shows at least one of a predicted and a historical blood plasma drug concentration of the drug over time.

25. The control of claim 22, wherein the memory stores effect compartment drug concentrations over time for the drug.

26. The control of claim 25, wherein the display is controlled by the processor to selectively display at least one of a predicted and a historical effect compartment drug concentration for the drug over time.

27. The control of claim 22, wherein the user interface includes a mode switch enabling the user to select between a manual mode and a PK model control mode for controlling the drug delivery system, said processor continuing to model and track at least one of a blood plasma drug concentration and an effect compartment drug concentration over time while operating in the manual mode, thereby enabling the processor to resume controlling administration of the drug in the PK model control mode if said mode is selected after control of the drug delivery system in the manual mode.

28. The control of claim 27, wherein the processor causes the display to show at least one of the blood plasma drug concentration and the effect compartment drug concentration during operation of the drug delivery system in the manual mode.

29. The control of claim 22, wherein the display shows at least one of a historical and a predicted blood plasma drug concentration level over time, and of a historical and a predicted effect compartment drug concentration over time, after delivery of the drug is terminated.

30. A method for controlling a multi-channel drug delivery system with which a plurality of drugs are selectively administered to a patient through a plurality of drug channels in accordance with a PK model, comprising the steps of:
   (a) enabling a user to input a plurality of parameters used by the PK model in controlling administration of a drug to the patient;
   (b) determining a drug concentration within the patient over time for each drug, as each drug is administered by the multi-channel drug delivery system:
      (i) during any interruption and after a termination of the drug delivery; and
      (ii) regardless of any change in the drug channel through which any drug is delivered.

31. The method of claim 30, further comprising the step of selectively modeling and controlling one of an effect compartment drug concentration for the plurality of drugs in the patient, and a blood plasma drug concentration for the plurality of drugs in the patient.

32. The method of claim 31, wherein the PK model controls an effect compartment drug concentration for each drug, further comprising the step of storing effect compartment drug concentrations over time for the plurality of drugs.

33. The method of claim 32, further comprising the step of selectively displaying at least one of a predicted and a historical effect compartment drug concentration over time for the plurality of drugs.

34. The method of claim 31, wherein the PK model controls a blood plasma drug concentration for each drug, further comprising the step of storing blood plasma drug concentrations over time for the plurality of drugs.

35. The method of claim 34, further comprising the step of selectively displaying at least one of a predicted and a historical blood plasma drug concentration for the plurality of drugs over time.

36. The method of claim 30, further comprising the steps of enabling the user to select between a manual mode and a PK model control mode for controlling delivery of any of the plurality of drugs by the multi-channel drug delivery system; and continuing to model and track at least one of a blood plasma drug concentration and an effect compartment drug concentration over time while operating in the manual mode, thereby enabling administration of a drug in the PK model control mode to occur if said mode is selected after the manual mode was used to control delivery of the drug by the multi-channel drug delivery system.

37. The method of claim 36, further comprising the step of displaying at least one of the blood plasma drug concentration and the effect compartment drug concentration over time, during operation of the multi-channel drug delivery system in the manual mode.

38. The method of claim 36, further comprising the step of displaying for the drug, at least one of a historical and a predicted blood plasma drug concentration level over time, and of a historical and a predicted effect compartment drug concentration over time:
   (a) after delivery of a drug is terminated; or
   (b) after a different drug is delivered in the same drug channel as said drug, and then delivery of said drug is resumed; or
   (c) after delivery of the drug is resumed in a different drug channel.

39. A method for controlling a multi-channel drug delivery system with which a plurality of drugs are selectively administered to a patient in accordance with a PK model, comprising the steps of:
   (a) enabling a user to input at least some of a plurality of parameters used by the PK model;
   (b) controlling administration of the plurality of drugs to the patient using the PK model; and
   (c) enabling the user to selectively determine whether the control uses the PK model to achieve either:
      (i) a desired blood plasma drag concentration; or
      (ii) a desired effect compartment drug concentration.

40. The method of claim 39, further comprising the step of storing blood plasma drug concentrations over time for the plurality of drugs.

41. The method of claim 40, further comprising the step of selectively displaying at least one of a predicted and a historical blood plasma drug concentration over time.

42. The method of claim 39, further comprising the step of storing effect compartment drug concentrations over time.

43. The method of claim 40, further comprising the step of selectively displaying at least one of a predicted and a historical effect compartment drug concentration over time.

44. The method of claim 39, further comprising the step of enabling the user to select between a manual mode and a PK model control mode for controlling the multi-channel drug delivery system; and continuing to model and track at least one of a blood plasma drug concentration and an effect compartment drug concentration over time while operating in the manual mode, thereby enabling administration of a drug in the PK model control mode to be used to control delivery of a drug if said mode is selected after the manual mode was used to control delivery of the drug.

45. The method of claim 44, further comprising the step of displaying at least one of the blood plasma drug concentration and the effect compartment drug concentration during operation of the multi-channel drug delivery system in the manual mode.

46. The method of claim 44, further comprising the step of displaying at least one of a historical and a predicted blood plasma drug concentration level over time, and of a historical and a predicted effect compartment drug concentration over time, after delivery of a drug is terminated.

47. The method of claim 39, further comprising the step of enabling the user to selectively determine whether a different PK model is used to control the delivery of different drugs.

48. A method for controlling a drug delivery system with which a drug is administered to a patient in accordance with a PK model, comprising:
   (a) enabling a user to input a plurality of parameters used by the PK model in controlling administration of the drug to the patient;
   (b) operating the drug delivery system to administer the drug to the patient in accordance with said parameters; and
   (c) selectively determining whether the control uses the PK model to achieve either:
      (i) a desired blood plasma drug concentration; or
      (ii) a desired effect compartment drug concentration within the patient.

49. The method of claim 48, further comprising the step of storing blood plasma drug concentrations over time for the drug.

50. The method of claim 49, further comprising the step of selectively displaying at least one of a predicted and a historical blood plasma drug concentration over time for the drug.

51. The method of claim 48, further comprising the step of storing effect compartment drug concentrations over time for the drug.

52. The method of claim 51, further comprising the step of selectively displaying at least one of a predicted and a historical effect compartment drug concentrations over time for the drug.

53. The method of claim 49, further comprising the steps of enabling the user to select between a manual mode and a PK model control mode for controlling the drug delivery system; and continuing to model and track at least one of a blood plasma drug concentration and an effect compartment drug concentration over time while operating in the manual mode, thereby enabling the processor to control administration of the drug in the PK model control mode if said mode is selected after the manual mode was used to control administration of the drug.

54. The method of claim 53, further comprising the step of displaying at least one of the blood plasma drug concentration and the effect compartment drug concentration during operation of the drug delivery system in the manual mode.

55. The method of claim 53, further comprising the step of displaying at least one of a historical and a predicted blood plasma drug concentration level over time, and of a historical and a predicted effect compartment drug concentration over time, after delivery of the drug is terminated.

* * * * *